United States Patent
Baldwin et al.

(10) Patent No.: US 9,364,351 B2
(45) Date of Patent: Jun. 14, 2016

(54) METHOD FOR FORMING A STENT

(75) Inventors: Matthew Baldwin, Santa Rosa, CA (US); Richard Bliss, Cloverdale, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 807 days.

(21) Appl. No.: 13/453,175

(22) Filed: Apr. 23, 2012

(65) Prior Publication Data
US 2013/0282107 A1  Oct. 24, 2013

(51) Int. Cl.
- B21F 3/04 (2006.01)
- A61F 2/88 (2006.01)
- B23K 26/00 (2014.01)
- A61F 2/915 (2013.01)

(52) U.S. Cl.
CPC ... *A61F 2/88* (2013.01); *B21F 3/04* (2013.01); *B23K 26/0075* (2013.01); *B23K 26/361* (2015.10); *A61F 2002/91558* (2013.01); *A61F 2240/001* (2013.01); *Y10T 29/49995* (2015.01)

(58) Field of Classification Search
CPC .............. Y10T 29/49995; A61F 2/88; A61F 2002/91558; A61F 2240/001; B21F 1/04; B21F 3/02; B21F 3/04; B21F 45/008
USPC .................................................. 72/306, 385
See application file for complete search history.

(56) References Cited

U.S. PATENT DOCUMENTS

| | | |
|---|---|---|
| 2,153,936 A | 4/1939 | Owens et al. |
| 3,185,185 A | 5/1965 | Pfund |
| 4,047,544 A | 9/1977 | Seaborn et al. |
| 4,886,062 A | 12/1989 | Wiktor |
| 5,019,090 A | 5/1991 | Pinchuk |
| 5,092,877 A | 3/1992 | Pinchuk |
| 5,133,732 A | 7/1992 | Wiktor |
| 5,226,913 A | 7/1993 | Pinchuk |
| 5,304,200 A | 4/1994 | Spaulding |
| 5,314,472 A | 5/1994 | Fontaine |
| 5,324,472 A | 6/1994 | Page et al. |
| 5,370,683 A | 12/1994 | Fontaine |
| 5,443,498 A | 8/1995 | Fontaine |
| 5,527,354 A | 6/1996 | Fontaine et al. |
| 5,549,663 A | 8/1996 | Cottone, Jr. |
| 5,653,727 A | 8/1997 | Wiktor |
| 5,716,396 A | 2/1998 | Williams, Jr. |
| 5,749,919 A | 5/1998 | Blanc |
| 5,895,406 A | 4/1999 | Gray et al. |
| 5,902,266 A | 5/1999 | Leone et al. |

(Continued)

FOREIGN PATENT DOCUMENTS

| | | |
|---|---|---|
| EP | 0565251 | 10/1993 |
| EP | 945107 | 9/1999 |

(Continued)

*Primary Examiner* — Debra Sullivan

(57) ABSTRACT

A method of forming a stent includes forming a wave form from a formable material. The wave form includes a plurality of substantially straight portions and a plurality of curved portions, each curved portion connecting adjacent substantially straight portions. The method includes wrapping the wave form around a mandrel at an angle to form a helical coil comprising a plurality of turns, connecting a first curved portion of a first turn to an adjacent second curved portion of a second turn at a position along the wave form to define an end of the stent, and removing excess material from an end of the wave form extending past the first curved portion while smoothing the end of the stent.

10 Claims, 5 Drawing Sheets

(56) References Cited

U.S. PATENT DOCUMENTS

| | | |
|---|---|---|
| 5,913,897 A | 6/1999 | Corso, Jr. et al. |
| 6,042,597 A | 3/2000 | Kveen et al. |
| 6,117,165 A | 9/2000 | Becker |
| 6,136,023 A | 10/2000 | Boyle |
| 6,190,406 B1 | 2/2001 | Duerig et al. |
| 6,203,569 B1 | 3/2001 | Wijay |
| 6,342,067 B1 | 1/2002 | Mathis et al. |
| 6,355,059 B1 | 3/2002 | Richter et al. |
| 6,423,091 B1 | 7/2002 | Hojeibane |
| 6,432,132 B1 | 8/2002 | Cottone et al. |
| 6,447,540 B1 | 9/2002 | Fontaine et al. |
| 6,503,270 B1 | 1/2003 | Richter et al. |
| 6,610,086 B1 | 8/2003 | Kock et al. |
| 6,656,219 B1 | 12/2003 | Wiktor |
| 6,730,117 B1 * | 5/2004 | Tseng et al. ............ 623/1.16 |
| 6,736,844 B1 | 5/2004 | Glatt et al. |
| 6,878,162 B2 | 4/2005 | Bales et al. |
| 6,923,828 B1 | 8/2005 | Wiktor |
| 6,969,402 B2 | 11/2005 | Bales et al. |
| 7,004,968 B2 | 2/2006 | Lootz et al. |
| 7,108,714 B1 | 9/2006 | Becker |
| 7,169,175 B2 | 1/2007 | Cottone, Jr. et al. |
| 7,329,277 B2 | 2/2008 | Addonizio et al. |
| 8,710,400 B2 * | 4/2014 | Briand et al. ............ 219/121.67 |
| 2002/0095208 A1 | 7/2002 | Gregorich et al. |
| 2003/0083736 A1 | 5/2003 | Brown et al. |
| 2004/0044401 A1 | 3/2004 | Bales et al. |
| 2004/0143318 A1 | 7/2004 | Tseng et al. |
| 2006/0030934 A1 | 2/2006 | Hogendijk et al. |
| 2006/0079955 A1 | 4/2006 | Brown |
| 2008/0097580 A1 | 4/2008 | Dave |
| 2008/0097582 A1 | 4/2008 | Shanley et al. |
| 2008/0183273 A1 | 7/2008 | Mesana et al. |
| 2008/0288053 A1 | 11/2008 | Addonizio et al. |
| 2008/0289389 A1 | 11/2008 | Fitch et al. |
| 2008/0294241 A1 | 11/2008 | Addonizio et al. |
| 2008/0306583 A1 | 12/2008 | Bashiri et al. |
| 2008/0319529 A1 | 12/2008 | Krivoruchko et al. |
| 2008/0319534 A1 | 12/2008 | Birdsall et al. |
| 2008/0319535 A1 | 12/2008 | Craven et al. |
| 2009/0005848 A1 | 1/2009 | Strauss et al. |
| 2009/0024207 A1 | 1/2009 | Addonizio et al. |
| 2009/0036976 A1 | 2/2009 | Beach et al. |
| 2011/0218614 A1 * | 9/2011 | Lam .................. A61F 2/88 623/1.15 |
| 2011/0264195 A1 * | 10/2011 | Griswold ............. 623/1.22 |

FOREIGN PATENT DOCUMENTS

| | | |
|---|---|---|
| EP | 1155664 | 11/2007 |
| GB | 2281865 | 3/1995 |
| WO | WO2007/095466 | 8/2007 |
| WO | WO2008/028964 | 3/2008 |
| WO | WO2008/049045 | 4/2008 |
| WO | WO2008/100783 | 8/2008 |
| WO | WO2011/109159 | 9/2011 |

* cited by examiner

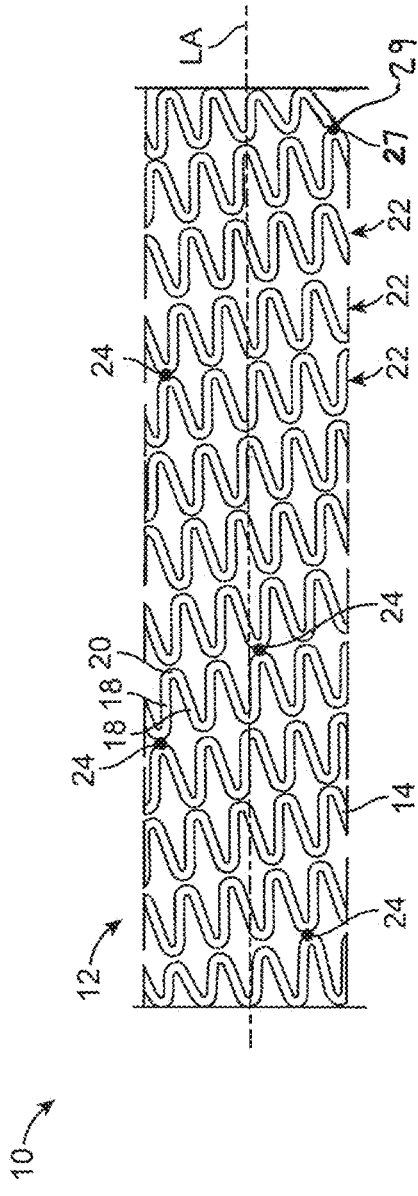
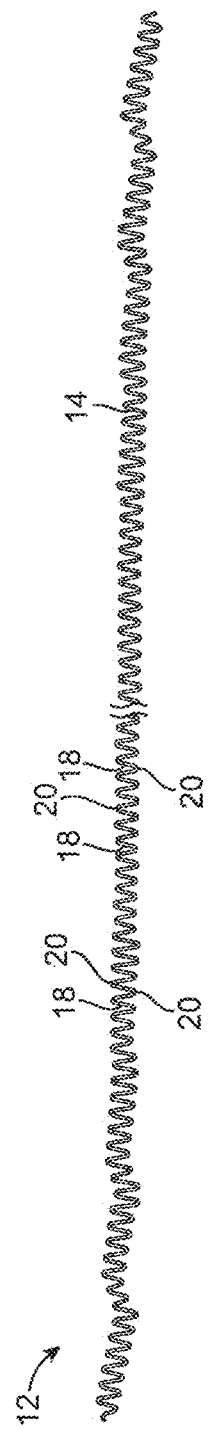

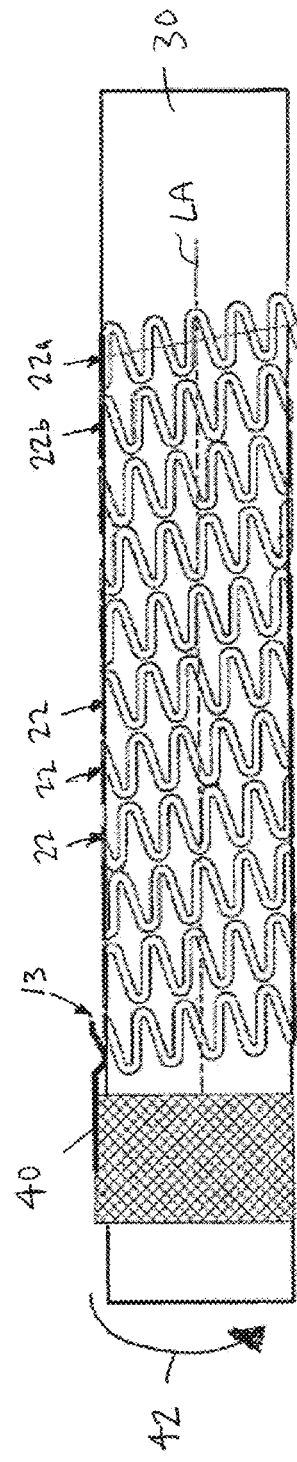
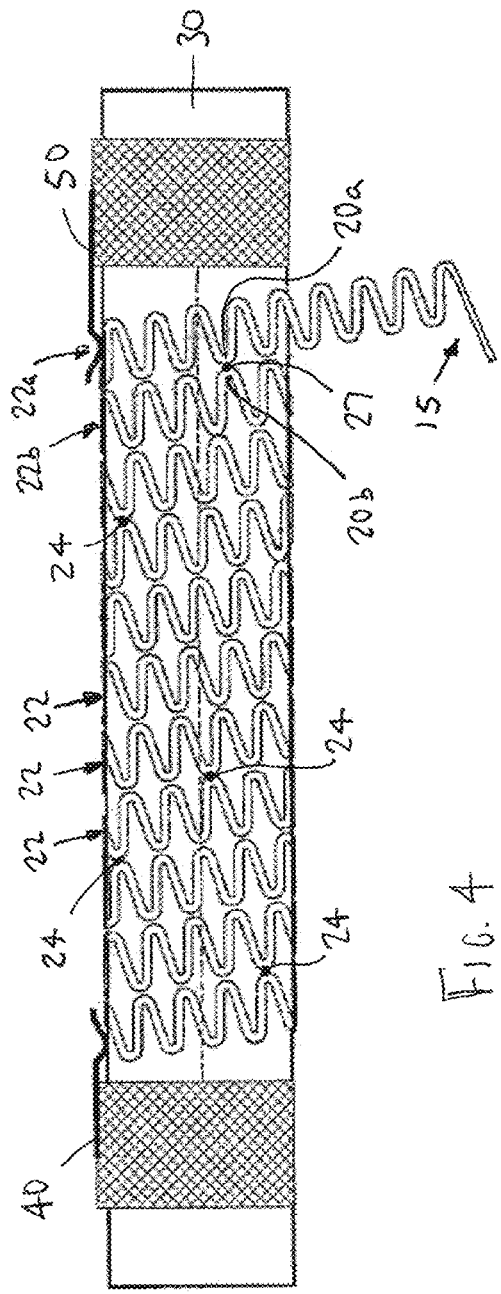
Fig. 3
Fig. 4

METHOD FOR FORMING A STENT

BACKGROUND OF THE INVENTION

1. Field of the Invention

The present invention is generally related to a method for forming a stent.

2. Background of the Invention

A stent is typically a hollow, generally cylindrical device that is deployed in a body lumen from a radially contracted configuration into a radially expanded configuration, which allows it to contact and support a vessel wall. A plastically deformable stent can be implanted during an angioplasty procedure by using a balloon catheter bearing a compressed or "crimped" stent, which has been loaded onto the balloon. The stent radially expands as the balloon is inflated, forcing the stent into contact with the body lumen, thereby forming a support for the vessel wall. Deployment is effected after the stent has been introduced percutaneously, transported transluminally, and positioned at a desired location by means of the balloon catheter.

Stents may be formed from wire(s) or strip(s) of material, may be cut from a tube, or may be cut from a sheet of material and then rolled into a tube-like structure. While some stents may include a plurality of connected rings that are substantially parallel to each other and are oriented substantially perpendicular to a longitudinal axis of the stent, others may include a helical coil that is wrapped or wound around a mandrel aligned with the longitudinal axis at a non-perpendicular angle.

Stent designs that are comprised of wound materials generally have complex geometries so that the final stents may be precisely formed. The small size and complexity of some stent designs generally makes its formation difficult. Wound stents are formed such that when unsupported, they create the desired stent pattern and vessel support. This process generally involves winding a source material around a supporting structure such as a rod or mandrel and creating a helical or spring-like wrap pattern. To provide greater support, along this wrapped element, geometries are formed into the source material to better support the tissue in between each wrap, usually of sinusoidal nature.

Stent designs that are comprised of wound materials generally have complex geometries so that the final stents may be precisely formed. The small size and complexity of some stent designs generally makes its formation difficult. Wound stents are formed such that when unsupported, they create the desired stent pattern and vessel support. This process generally involves winding a source material around a supporting structure such as a rod or mandrel and creating a helical or spring-like wrap pattern. To provide greater support, along this wrapped element, geometries are formed into the source material to better support the tissue in between each wrap, usually of sinusoidal nature. A potential down side to a wrapped stent is that the ends of the wound material that define the ends of the stent may have rough edges after excess material has been removed from the rest of the stent.

SUMMARY OF THE INVENTION

According to an aspect of the present invention, there is provided a method of forming a stent. The method includes forming a wave form from a formable material. The wave form includes a plurality of substantially straight portions and a plurality of curved portions, each curved portion connecting adjacent substantially straight portions. The method includes wrapping the wave form around a mandrel at an angle to form a helical coil comprising a plurality of turns, connecting a first curved portion of a first turn to an adjacent second curved portion of a second turn at a position along the wave form to define an end of the stent, and removing excess material from an end of the wave form extending past the first curved portion while smoothing the end of the stent.

According to an aspect of the present invention, there is provided a stent formed by a method that includes forming a wave form from a formable material. The wave form includes a plurality of substantially straight portions and a plurality of curved portions, each curved portion connecting adjacent substantially straight portions. The method includes wrapping the wave form around a mandrel at an angle to form a helical coil comprising a plurality of turns, connecting a first curved portion of a first turn to an adjacent second curved portion of a second turn at a position along the wave form to define an end of the stent, and removing excess material from an end of the wave form extending past the first curved portion while smoothing the end of the stent.

These and other aspects of the invention as well as the methods of operation and functions of the related elements of structure will become more apparent upon consideration of the following description and the appended claims with reference to the accompanying drawings, all of which form a part of this specification. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

Embodiments of the invention will now be described, by way of example only, with reference to the accompanying schematic drawings in which corresponding reference symbols indicate corresponding parts, and in which:

FIG. 1 is a schematic view of a stent after being formed by a method in accordance with an embodiment of the invention;

FIG. 2 is a schematic view of a wave form before the wave form is wound into the stent of FIG. 1;

FIG. 3 is a schematic view of the wave form of FIG. 2 being wrapped around a mandrel into a helical coil in accordance with an embodiment of the invention;

FIG. 4 is a schematic view of the helical coil of FIG. 3 being clamped to the mandrel;

DETAILED DESCRIPTION OF EMBODIMENTS OF THE INVENTION

Figure 5:
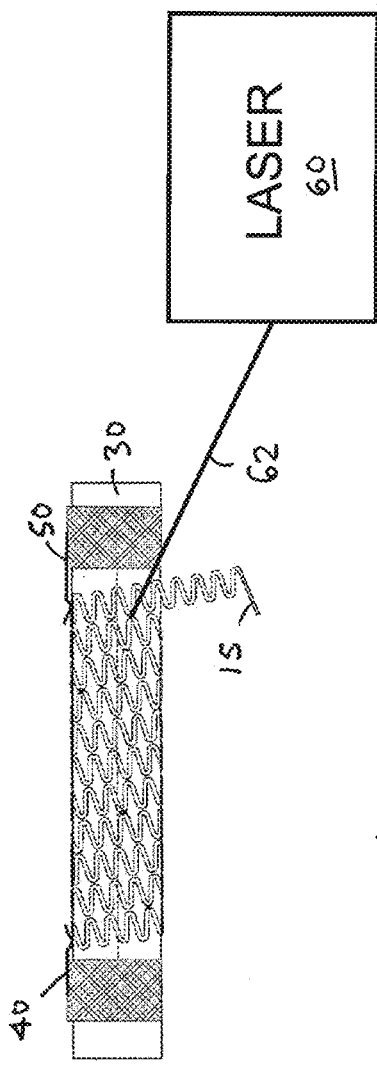
FIG. 5 is a schematic view of a laser generating a laser beam used to sever an end of the wave form from the helical coil in accordance with an embodiment of the invention.

The following detailed description is merely exemplary in nature and is not intended to limit the invention or the application and use of the invention. Furthermore, there is no intention to be bound by any expressed or implied theory presented in the preceding technical field, background, brief summary or the following detailed description.

FIG. 1 schematically illustrates a stent 10 that has been manufactured according to an embodiment of the present invention. The stent 10 is generally cylindrical in shape and has a longitudinal axis extending through the center of the stent 10. The stent 10 includes a continuous wave form 12 that is formed from a formable material 14 using a suitable forming apparatus.

As illustrated in FIG. 2, the wave form 12 may be formed so that the wave form 12 includes a plurality of struts 18 and a plurality of crowns 20. Each crown 20 is a curved portion or turn within the wave form 12 that connects adjacent struts 18 to define the continuous wave form 12. As shown in FIG. 2, the struts 18 are substantially straight portions of the wave form 12. In other embodiments, the struts 18 may be slightly bent or have other shapes, such as a sinusoidal wave, for example. The illustrated embodiment is not intended to be limiting in any way.

After the wave form 12 has been formed by the forming apparatus, the wave form 12 may be wrapped, at a pitch, around a mandrel 30 that has a longitudinal axis LA that will coincide with the longitudinal axis of the stent 10, so as to form a helical coil a constant helical angle, or pitch angle $\alpha$, having multiple turns 22, as illustrated in FIG. 3. One end 13 of the wave form 12 may be pressed against the mandrel 30 with a pressing member 40 that is attached to the mandrel 30 so that it rotates and translates with the mandrel 30. The other end 15 of the wave form 20 may be held with a suitable structure that is configured to hold the end 15 of the wave form 20 as the wave form 20 is wrapped around the mandrel 30 so that the helical angle $\alpha$ stays substantially constant.

The mandrel 30 may be rotated and translated, as indicated by arrows 42 and 44, respectively, at a suitable speed so that the wave form 20 wraps around the mandrel 30, and the longitudinal axis LA, to create the turns 22. The number of revolutions of the mandrel 30 determines the number of turns 22 in the stent 10.

After the helical coil has been formed, an end portion of the helical coil that is opposite the end being clamped to the mandrel 30 by the pressing member 40 may be clamped to the mandrel 30 with a second suitable pressing member 50 or clamp so that select crowns 20 of adjacent turns 22 may be connected together, as represented by connections 24 illustrated in FIG. 4. The connections 24 may be formed by fusing the select crowns 20 together, or by welding the select crowns 20 together, or by using any other suitable method to connect portions of adjacent turns 22 together. The location of the end of the stent may be determined, and a first crown 20a of a first turn 22a and a second crown 20b of a second turn 22b may be connected together with a connection 27 that will define the end of the stent 10. The connection 27 may be formed by fusing the first crown 20a and the second crown 20b together, or by welding the first crown 20a and the second crown 20b together, or by using any other suitable method to connect the first crown 20a and the second crown 20b together.

Figure 6:
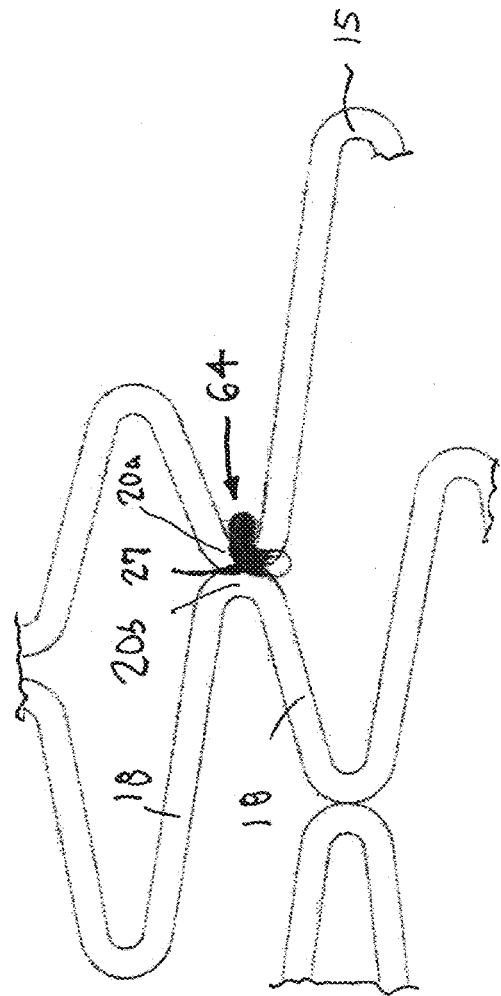
FIG. 6 is a schematic diagram illustrating a path of a laser beam used to sever the end of the wave form from the helical coil in accordance with an embodiment of the invention.

In order to finish off the ends of the stent, the excess wave form 12, such as the end 15 of the wave form 12 illustrated in FIG. 4, may be severed from the helical coil. In an embodiment, a laser 60 may be used to generate a laser beam 62 to melt the formable material at a location where it is desired to remove the end 15 of the wave form 12 from the remainder of the helical coil, as schematically illustrated in FIG. 5. The tension in the helical coil, which is clamped to the mandrel 30, causes the end 15 of the wave form to separate from the remaining portion of the wave form 12 that forms the helical coil as the laser beam 62 is directed along a path 64 illustrated in FIG. 6. The path 64 may generally be defined as starting at about a 90° angle with respect to the tangent of the second crown 20b, passing through the first crown 20a, then moving substantially parallel to the tangent of the second crown 20b, without touching the second crown 20b or any other part of the wave form 12.

Figure 7:
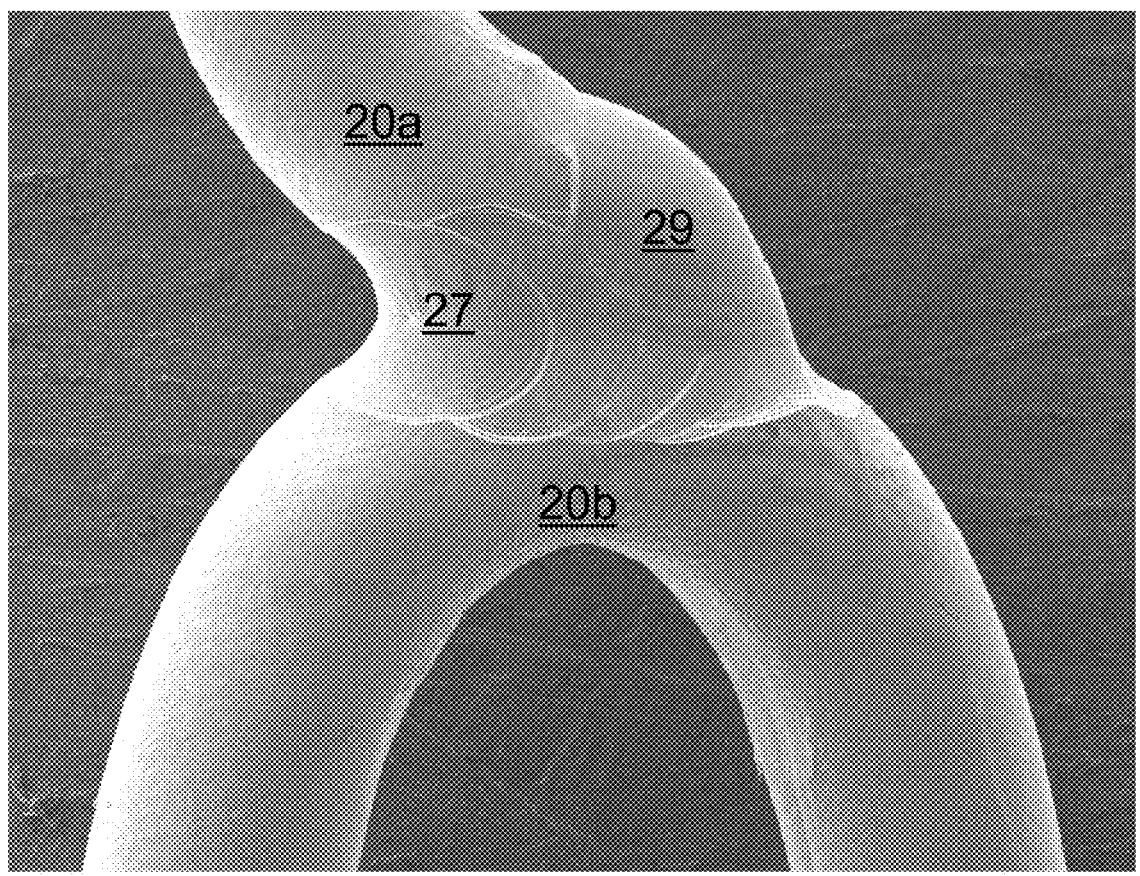
FIG. 7 is a photomicrograph of an end of the stent of FIG. 1 after the laser beam has been used to sever the end of the wave form from the helical coil and secure a new end of the wave form to an adjacent crown in the wave form.

The laser 60 may be a YAG, diode, solid state, $CO_2$, pulsed, continuous, fiber, or any other suitable type of laser. In an embodiment, a solid state, pulsed laser may be used. The laser 60 may travel along the path 64 at a speed of between 0.01 inches per second to 10 inches per second, and a pulse width of between 0.1 inch and 0.9 inch, depending on the frequency and power used. The frequency may be between 20 Hz and 200 Hz. The power of the laser may be between 1 W and 1 kW. Inert gas shielding, such as with argon, nitrogen, or helium may also be used. The heat provided by the laser beam 62 causes the formable material to melt, and even vaporize. As the laser beam 62 "cuts" the formable material, the laser beam 62 leaves a molten pool of material in its wake, which may reform into a smooth mass 29 upon cooling, as shown in FIG. 7. The same method may be used to terminate the other end 13 of the wave form 12 from the helical coil that defines the stent 10.

Figure 8:
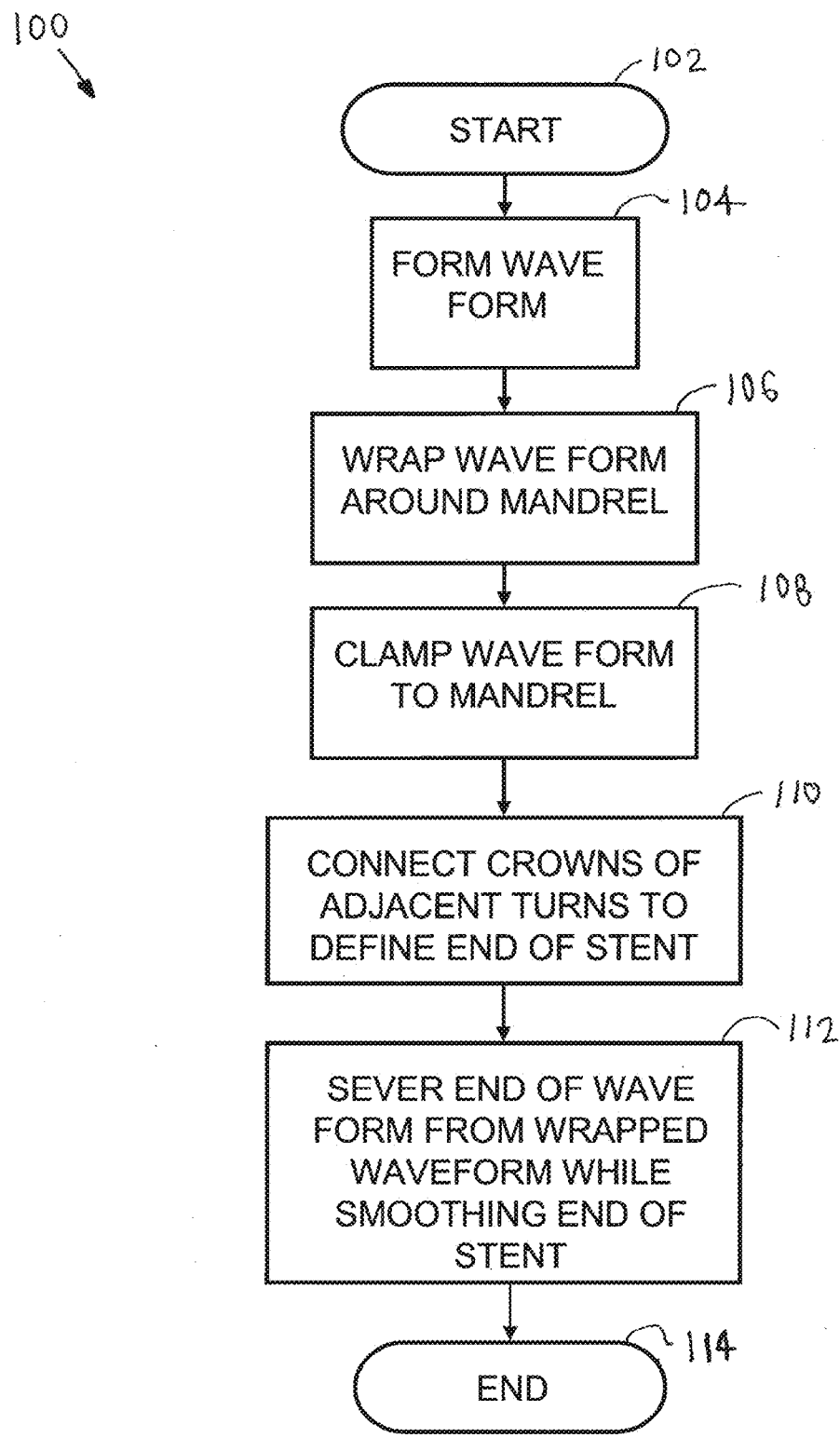
FIG. 8 is a flow chart of a method of forming the stent of FIG. 1, in accordance with an embodiment of the present invention.

FIG. 8 illustrates a method 100 for forming a stent, such as the stent 10 of FIG. 1, in accordance with an embodiment of the present invention. As illustrated, the method 100 starts at 102. The method includes forming a wave form, such as the wave form 12 illustrated in FIG. 2, at 104. After the wave form 12 is formed, at 106, the wave form 12 is wrapped around a mandrel, such as the mandrel 30 of FIG. 3, to form a helical coil. After the wave form 12 is wrapped around the mandrel 30, the resulting helical coil is clamped to the mandrel 30 at 108. At 110, the method includes connecting a crown from a first turn of the wrapped wave form to a crown from a second turn of the wrapped wave form to define an end of the stent. After the crowns have been connected, the end 15 of the wave form 12 severed from the wrapped wave form while what is now the end of the stent is smoothed at 112. The method ends at 114. As understood by one of skill in the art, the method 100 may repeat 110 and 112 for the other end of the stent. In an embodiment, the stent may then be subject to further post processing steps know in the art, such as annealing, polishing, etc.

Embodiments of the stents made using the method and apparatus discussed above may be formed from a sheet, roll, or strip of suitable formable material. In certain embodiments, the stent may be formed, i.e., etched or cut, from a thin tube of suitable material, or from a thin plate of suitable material and rolled into a tube. Suitable materials for the stent include but are not limited to stainless steel, iridium, platinum, gold, tungsten, tantalum, palladium, silver, niobium, zirconium, aluminum, copper, indium, ruthenium, molybdenum, niobium, tin, cobalt, nickel, zinc, iron, gallium, manganese, chromium, titanium, aluminum, vanadium, carbon, and magnesium, as well as combinations, alloys, and/or laminations thereof. For example, the stent may be formed from a cobalt alloy, such as L605 or MP35N®, Nitinol (nickel-titanium shape memory alloy), ABI (palladium-silver alloy), Elgiloy® (cobalt-chromium-nickel alloy), etc. It is also contemplated that the stent may be formed from two or more materials that are laminated together, such as tantalum that is laminated with MP35N® alloy, or from a filled or coextruded wire having one material in the center of the wire that is surrounded by another material. The stents may also be formed from sheets, rolls, or strips of material having layers of different metals, alloys, or other materials. Embodiments of the stent may also be formed from hollow material that has been filled with other materials. The aforementioned materials and laminations are intended to be examples and are not intended to be limiting in any way.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient roadmap for implementing an exemplary embodiment of the invention, it being understood that various changes may be made in the function and arrangement of members described in an exemplary embodiment without departing from the scope of the invention as set forth in the appended claims.

What is claimed is:

1. A method of forming a stent, the method comprising:
    forming a wave form from a formable material, the wave form comprising a plurality of substantially straight portions and a plurality of curved portions, wherein each curved portion has a crown, each curved portion connecting adjacent substantially straight portions;
    wrapping the wave form around a mandrel at an angle to form a helical coil comprising a plurality of turns;
    connecting a first crown of a first curved portion of a first turn to an adjacent second crown of a second curved portion of a second turn at a position along the wave form, wherein an end portion of the wave form extends past the first curved portion; and
    severing the end portion of the wave form from the helical coil at the first crown to define an end of the stent.

2. The method according to claim 1, wherein a laser beam generated by laser is used to remove the end portion of the wave form.

3. The method according to claim 2, wherein the laser beam melts the formable material to form a molten pool that reforms into a smooth mass upon cooling.

4. The method according to claim 2, wherein said severing comprises moving the laser beam along a path that avoids contact with a portion of the wave form that defines the stent.

5. The method according to claim 4, wherein the path passes through the first curved portion of the first turn at an angle substantially perpendicular to a tangent of the second curved portion of the second turn.

6. The method according to claim 5, wherein after the path passes through the first curved portion, the path extends substantially parallel to the tangent of the second curved portion without touching the second curved portion.

7. The method according to claim 4, wherein the laser beam moves along the path at a speed of between 0.01 inch/second and 10 inches/second.

8. The method according to claim 4, wherein the laser beam has a pulse width of between 0.1 inch and 0.9 inch.

9. The method of claim 1, further comprising connecting selected curved portions of the wave form in adjacent turns of the helical coil.

10. A stent formed in accordance with the method of claim 1.

* * * * *